United States Patent
Engel et al.

(10) Patent No.: US 12,324,649 B2
(45) Date of Patent: Jun. 10, 2025

(54) DETERMINING A TISSUE TYPE OF A TISSUE OF AN ANIMAL OR HUMAN INDIVIDUAL

(71) Applicant: Siemens Healthcare GmbH, Erlangen (DE)

(72) Inventors: Thomas Engel, Aalen (DE); Alexander Michael Gigler, Untermeitingen (DE); Clemens Otte, Munich (DE); Remigiusz Pastusiak, Munich (DE); Tobias Paust, Leipheim (DE); Elfriede Simon, Munich (DE); Evamaria Stütz, Munich (DE); Stefanie Vogl, Konzell (DE)

(73) Assignee: Siemens Healthineers AG, Forchheim (DE)

( * ) Notice: Subject to any disclaimer, the term of this patent is extended or adjusted under 35 U.S.C. 154(b) by 923 days.

(21) Appl. No.: 16/336,903

(22) PCT Filed: Sep. 27, 2017

(86) PCT No.: PCT/EP2017/074488
§ 371 (c)(1),
(2) Date: Mar. 26, 2019

(87) PCT Pub. No.: WO2018/060243
PCT Pub. Date: Apr. 5, 2018

(65) Prior Publication Data
US 2020/0029818 A1   Jan. 30, 2020

(30) Foreign Application Priority Data
Sep. 27, 2016 (DE) .................. 10 2016 218 520.9

(51) Int. Cl.
| A61B 5/00 | (2006.01) |
| G06T 7/00 | (2017.01) |
| G06V 20/69 | (2022.01) |

(52) U.S. Cl.
CPC .......... *A61B 5/0075* (2013.01); *A61B 5/0071* (2013.01); *A61B 5/7267* (2013.01);
(Continued)

(58) Field of Classification Search
CPC ... A61B 5/0075; A61B 5/0071; A61B 5/7267; A61B 5/7264; A61B 5/007;
(Continued)

(56) References Cited

U.S. PATENT DOCUMENTS

| 5,999,844 A | 12/1999 | Gombrich |
| 6,109,270 A * | 8/2000 | Mah ........................ A61B 90/11 128/924 |

(Continued)

FOREIGN PATENT DOCUMENTS

WO   WO2015154187 A1   10/2015

OTHER PUBLICATIONS

B. Longstaff, S. Reddy and D. Estrin, "Improving activity classification for health applications on mobile devices using active and semi-supervised learning," 2010 4th International Conference on Pervasive Computing Technologies for Healthcare, 2010, pp. 1-7. (Year: 2010).*

(Continued)

*Primary Examiner* — Oommen Jacob
(74) *Attorney, Agent, or Firm* — Lempia Summerfield Katz LLC

(57) ABSTRACT

The invention relates to a method for determining a tissue type of a tissue of an animal or human individual, in which method: electromagnetic radiation (26) emitted by a tissue sample (24) of the tissue is sensed (10) by means of a
(Continued)

radiation sensor (22), the radiation sensor (22) providing a sensor signal (28) in accordance with the sensed electromagnetic radiation, and the sensor signal (28) is evaluated (12) by means of an evaluation unit (30) in order to determine and output the tissue type. The problem addressed by the invention is that of enabling improved determination of the tissue type. According to the invention, the evaluation unit (30) is a self-learning evaluation unit (30) that is initially trained (14) by means of training data sets (32) on the basis of at least one model, which is based on a method for machine learning, the training of the evaluation unit being conducted by means of such training data sets (32) each comprising a training sensor signal with an associated training tissue type.

9 Claims, 2 Drawing Sheets

(52) U.S. Cl.
CPC .............. *G06T 7/0012* (2013.01); *G06V 20/69* (2022.01); *G06T 2207/10048* (2013.01); *G06T 2207/20081* (2013.01); *G06T 2207/30024* (2013.01)

(58) Field of Classification Search
CPC ......... G06T 7/0012; G06T 2207/10048; G06T 2207/20081; G06T 2207/30024; G06T 2207/2008; G06V 20/69; G16H 50/70; G06K 9/6217
See application file for complete search history.

(56) References Cited

U.S. PATENT DOCUMENTS

| | | | | |
|---|---|---|---|---|
| 6,718,196 | B1* | 4/2004 | Mah | A61B 34/32 600/117 |
| 7,440,793 | B2* | 10/2008 | Chauhan | A61B 90/36 600/437 |
| 2005/0010102 | A1* | 1/2005 | Marchesini | A61B 5/0059 128/920 |
| 2006/0013454 | A1* | 1/2006 | Flewelling | G06T 11/00 382/128 |
| 2011/0289036 | A1* | 11/2011 | Stojadinovic | G16B 40/30 706/45 |
| 2015/0011893 | A1* | 1/2015 | Lui | A61B 5/7264 600/476 |
| 2015/0085279 | A1* | 3/2015 | Balooch | G16H 40/67 356/306 |
| 2016/0080665 | A1* | 3/2016 | Barnes | H04N 23/71 600/407 |
| 2016/0361121 | A1* | 12/2016 | Reicher | G06F 3/0482 |
| 2017/0020460 | A1 | 1/2017 | Leblond | |
| 2020/0029818 | A1* | 1/2020 | Engel | G06F 18/21 |

OTHER PUBLICATIONS

S.-K. Pavani, F. M. Sukno, D. Delgado-Gomez, C. Butakoff, X. Planes and A. F. Frangi, "An Experimental Evaluation of Three Classifiers for use in Self-Updating Face Recognition Systems," in IEEE Transactions on Information Forensics and Security, vol. 7, No. 3, pp. 932-943, Jun. 2012. (Year: 2012).*

PCT International Search Report and Written Opinion of International Searching Authority mailed Jan. 17, 2018, corresponding to PCT International Application No. PCT/EP2017/074488 filed Sep. 27, 2017.

Q. T. Nguyen, R. Y. Tsien, "Fluorescence-guided surgery with live molecular navigation—a new cutting edge," Nat Rev Cancer, 2013, vol. 13, Nr. 9, pp. 653-662, doi: 10.1038/nrc3566.

Ni, Wangdong, Lars Nørgaard, and Morten Mørup. "Non-linear calibration models for near infrared spectroscopy." Analytica chimica acta 813 (2014): 1-14.

Wikipedia: "Online machine learning—Wikipedia" Retrieved Dec. 2, 2023. pp. 1-11, Internet: URL:https/a://en.wikipedia.org/w/index.php?title=Online_machine_learning&oldid=738921530.

Wikipedia: "Online machine learning—Wikipedia"; Retrieved Aug. 4, 2014. pp. 1-5. Internet: URL:http/a://en.wikipedia.org/wiki/Online_machine_learning.

* cited by examiner

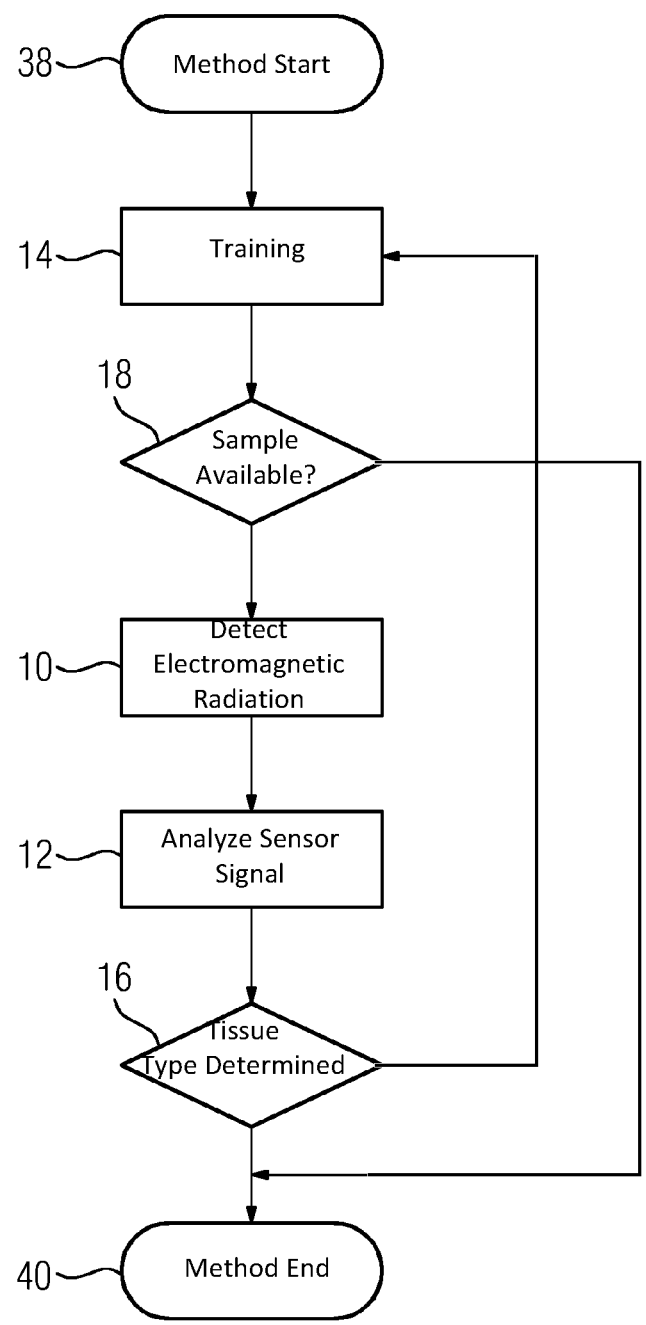

DETERMINING A TISSUE TYPE OF A TISSUE OF AN ANIMAL OR HUMAN INDIVIDUAL

This application is the National Stage of International Application No. PCT/EP2017/074488, filed Sep. 27, 2017, which claims the benefit of German Patent Application No. 10 2016 218 520.9, filed Sep. 27, 2016. The entire contents of these documents are hereby incorporated herein by reference.

BACKGROUND

The present embodiments relate to determining a tissue type of a tissue of an animal or a human individual.

For a surgical procedure in the body of the individual by the surgeon, who is normally a doctor, the visual impression on the surgeon and the expertise and experience of the surgeon are vital to deciding how the surgical procedure shall be carried out. It is important that the surgeon identifies which tissue types are situated at the location at which the surgical procedure is performed, identifies the condition of the tissue concerned, and establishes whether the tissue that is present exhibits changes that are inflammatory, necrotic, or malignant in nature or caused by injury. Such tissues are referred to as "abnormal tissue". Should abnormal tissue be present, based on the visual impression made on the surgeon, the surgeon is to use his judgment to decide how much of any abnormal tissue that may be present is to be removed, where a border between normal, healthy tissue and abnormal tissue lies, and, if applicable, how much of the normal or healthy tissue is to be removed in order to provide the best conditions for rapid recovery of the individual or patient.

Crucial factors influencing the view and the decision of the surgeon regarding removal of tissue are a severity and a macroscopically discernible difference of the abnormal tissue with respect to the healthy or normal tissue, and the visibility and accessibility of the operation area on the individual or region in which the surgical procedure takes place.

In such surgical procedures, it is often difficult for the surgeon to be able to distinguish a macroscopic structure of abnormal tissue (e.g., a tumor or the like) from normal or healthy tissue. It proves particularly difficult for the surgeon to decide purely based on his visual impressions where a border lies between normal or healthy tissue and abnormal tissue (e.g., malignant tissue) and whether, for example, for a tumor section, all the margins of the tumor are also actually removed entirely.

For example, if a tumor is resected, it is now standard practice to send the removed tissue directly to a pathology laboratory, where a histological examination is performed on the removed tissue immediately in order to be able to establish whether the removed tissue actually contains edges of the removed tumor, and thus, whether the complete tumor may have been removed. If it is ascertained in the examination that the tumor may not have been removed entirely, the surgeon is immediately notified of this so that the surgeon may suitably remove further tissue in order to be able to also include tumor edges not removed so far. The surgical procedure or operation is paused for the time taken by the histological examination, and the individual continues to be kept under anesthetic during this time until a final result of the histological examination is available.

The visual, macroscopic evaluation of the tissue proves particularly difficult if the region of the surgical procedure, or operation area, is visible only with difficulty (e.g., if the tumor is positioned directly beside or in vital organs or tissue, such as the brain or the like). Difficulties may be compounded further if the tumor is hidden by bone as well (e.g., by a skull).

The surgeon may rely largely on experience to interpret the visual image in the field of view and hence to identify what tissue type is present (e.g., whether the existing tissue is normal tissue, such as healthy tissue, or abnormal tissue, such as tumor tissue). For example, the surgeon uses experience to determine a border between normal or healthy tissue and abnormal tissue that is meant to be removed.

Haptic impressions of the tissue concerned may support the visual impression gained by the surgeon. This uses the knowledge that different tissue types (e.g., also differences between normal or healthy tissue and abnormal tissue such as tumor tissue) may sometimes exhibit differences in hardness or firmness.

For a tumor resection, during the operation or surgical procedure, a histological examination or assessment of the removed tissue, for example, is performed by rapid intra-operative biopsies, from which the pathologist may determine whether tumor borders have actually been captured (e.g., completely captured), or whether tumor tissue is still left behind in the individual. The surgical procedure or operation is paused during the time that this takes, and the individual continues to be kept under anesthetic.

To perform the surgical procedure or operation, the surgeon is to have the best possible view of the operation area, which provides that a wound arising from the surgical procedure or operation may be relatively large. This may place a great strain on the individual (e.g., as a result of a long and deep anesthetic, heavy blood loss, and/or the like), which may be detrimental to a subsequent healing process for the individual.

One possible way of minimizing the size of the wound caused by an operation or surgical procedure may be achieved by an endoscopic operation, which constitutes a minimally invasive operation. This type of operation is now used as standard in some areas (e.g., in neurosurgical procedures such as operating on a spinal disk, treatments of hydrocephalus, such as in an abdominal procedure such as an operation on the appendix, the gall bladder, for a hernia, or in procedures on joints, known as arthroscopy procedures, and/or the like). In an endoscopic operation, the surgical and/or optical instruments are inserted into the body of the individual through thin metal ducts. A camera (e.g., in the region of a tip of the endoscope) may provide visually from the body of the individual an image that may be displayed (e.g., by a display device such as a monitor, or the like).

An operating microscope is another tool for helping the surgeon get better visibility of the region of the operation or surgical procedure. The operating microscope is normally arranged above the region of the operation or surgical procedure, and may show this region in a suitably magnified form (e.g., with a magnification of up to about 40 times or similar). The magnification may be adjusted (e.g., at a lens and/or digitally by displaying on a monitor or the like). The operating microscope may thereby assist the surgeon with a more accurate specification of the tissue in terms of tissue type.

A further improvement may be achieved by using a fluorescence microscope as the operating microscope. This may exploit properties of fluorescent dyes, which either are administered to the individual in advance, or are applied during the operation or surgical procedure topically to the location under examination. Specific coloration (e.g., of tumor tissue) may be achieved inter-operatively using a suitable fluorescent dye (e.g., 5-aminolevulinic acid (5-ALA)), and this discoloration may then be made visible to the surgeon using the fluorescence microscope. Q. T. Nguyen et al., for example, disclose such a method in "Fluorescence-guided surgery with live molecular navigation—a new cutting edge" in HHS Public Access in PMC 2015, May 11.

When 5-ALA is used, tumor cells appear under the fluorescence microscope as red cells. This substance does not accumulate in non-tumor cells, which therefore, are not visible as red cells. Fluorescent dyes have the advantage of making differences that the surgeon would not be able to detect without such dyes clearly visible (e.g., a difference between tumor tissue and non-tumor tissue or the like). The otherwise invisible, or only poorly visible, differences may thus be made easier to see. This may help the surgeon to identify the border between normal or healthy tissue and tumor tissue, so that tumor tissue may be removed with greater certainty and more efficiently.

For fluorescent dyes, however, the uptake of these substances may put a strain on the individual or patient. There are only very few dyes approved (e.g., for humans) because these dyes mostly cause, or may cause, side effects. An example of one such substance in research on the animal model is Acriflavine, which is used as a fluorescent dye to assist imaging. Since this fluorescent dye may interact with the DNA of a cell, this fluorescent dye may act as a mutagen and therefore is not approved for use with humans.

In addition, devices that may combine the advantages of the endoscopic operation and the operating microscope are known (e.g., the Cellvisio apparatus from the company Mauna Kea). In this case, endoscopic in-vivo fluorescence colorations of tissue under examination may be detected.

SUMMARY AND DESCRIPTION

The scope of the present invention is defined solely by the appended claims and is not affected to any degree by the statements within this summary.

Although the prior art has hitherto proved successful, there is still a further need for improvement. There continues to be great uncertainty especially when determining tissue types (e.g., depending on the individual case concerned). Thus, there is a need to be able to determine the tissue type more reliably.

The present embodiments may obviate one or more of the drawbacks or limitations in the related art. For example, improved determination of a tissue type is facilitated.

With regard to a method of the type in question, the analysis unit is a self-learning analysis unit that is initially trained using training datasets based on at least one model based on a machine learning method. The training of the analysis unit is performed using the training datasets, which each includes a training sensor signal with an associated training tissue type.

With regard to a use of the type in question, a method of the present embodiments may be used.

With regard to the computer program product, this product may include a computer program for a processing unit of an analysis unit. The computer program includes program code segments of a program for performing the acts in accordance with the method of the present embodiments when the computer program is executed by the processing unit, so that by analyzing a sensor signal provided by a radiation sensor detecting electromagnetic radiation from a tissue sample, the analysis unit determines a tissue type of the tissue sample.

In terms of the device, for a device of the type in question, the analysis unit is a self-learning analysis unit configured to be trained initially using training datasets based on at least one model based on a machine learning method. The training of the analysis unit is performed using the training datasets, which each includes a training sensor signal with an associated training tissue type.

The present embodiments exploit the opportunity of using technical aids to assist the surgeon intra-operatively in assessing and identifying different tissue types, and/or in distinguishing between a normal, healthy, or benign tissue and abnormal tissue (e.g., tumor tissue). This may be done by using spectroscopy (e.g., infrared spectroscopy, ultraviolet spectroscopy, combinations thereof, and/or the like).

Infrared spectroscopy, for example, may be used to assist in distinguishing between tissue types or between substances based on corresponding molecular composition. This exploits the knowledge that functional groups of molecules respond differently as a result of light stimulation in the infrared spectral region, and thus, a spectral analysis yields characteristic differences. This may be used accordingly to obtain characteristic spectra that exhibit tissue-specific or substance-specific differences. Each individual spectrum may be associated with precisely one tissue type, so that it is possible to reach a simple decision between healthy or normal tissue and abnormal tissue (e.g., tumor tissue). Regarding infrared spectroscopy, additional reference is made, for example, to Wangdong Ni et al., "Non-linear calibration models for near infrared spectroscopy," Analytica Chimica Acta 813 (2014) 1-14.

It proves a problem here, however, that the molecular composition or molecular structure of normal or healthy tissue and of abnormal tissue (e.g., tumor tissue) arising from such tissue is very similar, so that although differences emerge in terms of measured spectra or infrared spectra, these differences may not always be attributed to individual known molecular differences that may be used as "intrinsic markers" for a specific tissue type. Such a difference at the molecular level that may distinguish between benign tissue and tumor tissue, for example, and that may also be verified by infrared spectroscopy is not known as yet.

Apart from different tissue types and/or the tissue conditions thereof, however, there may also be individual differences that may produce variations in the spectrum (e.g., in the infrared spectrum). For example, an infrared spectrum of a liver of a first individual may be different from an infrared spectrum of the liver of a second individual. Thus, the infrared spectrum need not be identical, but instead, individual-specific variations may occur. Circumstances relating to detecting the electromagnetic radiation (e.g., the infrared radiation) emitted by the tissue sample may also produce spectral variations, and thus, for example, an angle of incidence of the electromagnetic radiation applied to the tissue sample (e.g., an angle of incidence of light such as infrared light).

In order to assist the surgeon with, for example, the use of spectroscopy (e.g., infrared spectroscopy), an analysis method of one or more of the present embodiments may be implemented by an analysis unit and allows a sensor signal provided by the radiation sensor to be analyzed such that the detected electromagnetic radiation not only may be analyzed spectrally but, despite only small differences in the spectrum, may be associated uniquely with a particular, specific tissue type or to corresponding different conditions using the self-learning analysis unit. It may thus, for example, be identified whether the tissue is inflammatory, necrotic, benign, malignant, and/or such like.

The self-learning analysis unit is initially trained using training datasets based on at least one model. The model may be formed, for example, by one or more neural networks, partial least squares, kernel-based methods, and/or other machine learning methods. The analysis unit may include a hardware circuit that, for example, may include a programmable processing unit. The processing unit is controlled by a computer program such that the processing unit is capable of providing the desired functionality.

The analysis unit is trained using the training datasets, which each includes a training sensor signal with an associated training tissue type. In one embodiment, a large number of training datasets are used to train the self-learning analysis unit.

The training datasets may be obtained from tissue samples in vivo or in vitro. The training datasets may include data from a plurality of different individuals and/or from as many different tissue types as possible. The training datasets may be stored in a suitable database that is in communication with the analysis unit. The analysis unit may also include at least some of the database. The hardware circuit (e.g., the programmable processing unit) may then use a suitable algorithm to achieve reliable association of a sensor signal with a tissue type.

In order to be able to assist the surgeon during the surgical procedure or operation, the sensor signals provided by the radiation sensor may be analyzed computationally and promptly so as to be able to determine respective specific tissue types. This may, for example, be done during a tumor resection in order to achieve the operation as efficiently as possible and with as few side-effects as possible for the individual or patient.

The tissue may be a biological tissue of the individual, who may be an animal or a human, for example. The tissue may vary in consistency (e.g., elastic, firm, fluid, and so on). Possible examples of a fluid tissue are blood, liquor, and/or the like. The tissue may be organic tissue (e.g., a liver tissue, intestinal tissue, muscle tissue, or the like), or the tissue may also be connective tissue, fatty tissue, and/or the like.

The tissue sample emits electromagnetic radiation. The emitted electromagnetic radiation may be produced and emitted by the tissue sample per se. It may also be the case, however, that the tissue sample is stimulated to emit the electromagnetic radiation. For example, the stimulation may be by electromagnetic excitation radiation (e.g., light such as infrared light, ultraviolet light, combinations thereof, and/or the like). The tissue sample may reflect and/or transmit the excitation radiation. The tissue sample may also modify or convert the excitation light at least partially (e.g., in terms of spectral properties, a specific radiation intensity, and/or the like).

The radiation sensor is suitably configured for detecting the electromagnetic radiation. If the radiation sensor is meant to be used to detect infrared radiation or infrared light, for example, the radiation sensor may be configured as an infrared sensor. If the radiation sensor is meant to be able to detect ultraviolet light or ultraviolet radiation, for example, the radiation sensor may be configured as an ultraviolet sensor. Other regions of the electromagnetic radiation may be used as well. Also practically any combinations thereof may be provided.

The radiation sensor provides the sensor signal, which is dependent on the detected electromagnetic radiation. The radiation sensor is configured to detect a predetermined spectral band of the electromagnetic radiation to be detected. The sensor signal is provided by the radiation sensor accordingly. The sensor signal therefore contains information about the spectral distribution of the detected electromagnetic radiation.

The sensor signal is analyzed by the analysis unit. In one embodiment, in this regard, the sensor signal undergoes a spectral analysis. The spectral analysis may be performed, for example, by a Fourier transform or the like. A Laplace transform, Z-transform, and/or the like may also be provided depending on the type of signal. If the analysis is meant to be performed digitally (e.g., using a processing unit), the sensor signal may first be digitized in a suitable manner in order then to perform a suitable spectral analysis likewise digitally. Using the database, the tissue type may then be determined from the spectrum obtained in this way or from a spectral distribution of the detected electromagnetic radiation.

The self-learning analysis unit, which has already been pre-trained initially using the training datasets, is used for this purpose. Since, as already explained, spectral differences between different tissue types may be very small, it is typically not possible in practice to achieve a direct association based on a conventional database containing stored datasets. The self-learning functionality of the analysis unit may make the functionality of the analysis unit far more sensitive in this respect. As a result of this, it is possible to improve and/or make more reliable the association of a particular tissue type to a particular detected sensor signal. Specifically, high reliability in determining the tissue type may be achieved if the self-learning analysis unit is sufficiently well trained.

Since one or more of the present embodiments also allow a prompt examination of the tissue sample with regard to the tissue type, one or more of the present embodiments may be used to achieve reliable assistance to the surgeon even during the operation on the individual. It is thus no longer necessary to send the removed tissue to a separate histological examination center, which then performs a time-consuming examination and communicates relevant information about the determined tissue type to the surgeon, during which process, in the prior art, the individual is to continue to be under anesthetic. The associated risks may hence largely be avoided by using one or more of the present embodiments.

The tissue sample may contain a marker agent that influences the electromagnetic radiation emitted by the tissue sample. For example, the marker agent may stimulate the tissue to emit the electromagnetic radiation. It may even be the case that the marker agent itself emits the electromagnetic radiation. The marker agent may be a substance, for example, that behaves in a tissue-specific manner (e.g., accumulates preferentially in a specifically defined tissue). It may also be the case, however, that the marker agent is added during the operation and adheres solely to a specifically defined tissue. The marker agent may have specific properties regarding the emission of, or effect on, electromagnetic radiation, so that the marker simplifies detection of a specific tissue type. For example, the marker agent may itself emit electromagnetic radiation (e.g., infrared light or the like). It may also be the case that the marker agent may be stimulated to emit electromagnetic radiation by excitation radiation (e.g., excitation light). It may be provided, for example, that the marker agent converts the excitation radiation into predetermined emitted electromagnetic radiation. It may also be the case that the marker agent encourages or amplifies the emission of electromagnetic radiation by the tissue sample.

In one embodiment, the training datasets include specifiable training tissue types of animals and/or humans. The training tissue types are associated with the training sensor signals. It may thereby be achieved that the self-learning analysis unit may be trained particularly well by training datasets from as large a range as possible of individuals. This may take account of the fact that a large number of training datasets are often needed for training the self-learning analysis unit, and this number may not be achieved by a single individual.

In one embodiment, the specifiable training tissue types include healthy tissue and/or tumor tissue. It is thereby possible for the self-learning analysis unit to be trained in the area of distinguishing between healthy tissue and tumor tissue.

After determining the tissue type of the tissue sample, the analysis unit may be retrained taking into account a dataset associated with this analysis. The functionality of the analysis unit may thus be improved further during the intended operation.

In one embodiment, after each determination of a tissue type, the underlying dataset is used to retrain the analysis unit. The retraining may also be performed at definable times or at predetermined maintenance intervals. For this purpose, the relevant datasets may be stored separately until the training is carried out. The relevant datasets may also form new training datasets. The retraining may be also implemented during the intended use (e.g., during an operation). The self-learning analysis unit may be adapted quickly to specific situations that may arise during an operation on an individual. It is thus possible to improve further the functionality of the self-learning analysis unit (e.g., also the assistance to the surgeon) by the present embodiments.

In one embodiment, before determining the tissue type of the tissue sample, the analysis unit is trained using at least one additional known dataset from the same individual. For example, this dataset may be generated before an operation by providing an appropriate tissue sample from the individual and examining the tissue sample using the method according to one or more of the present embodiments (e.g., as part of a biopsy or the like). A plurality of tissue samples from the individual may be examined correspondingly before the planned operation, in order that the functionality of the self-learning analysis unit may be adapted particularly effectively to the individual. This may improve the intended assistance to the surgeon during the surgical procedure or operation. It allows in-vivo tissue samples and also ex-vivo tissue samples to be used. Thus, ex-vivo tissue samples from different individuals, which have undergone a pathology examination, may also be used for the training. This proves advantageous for the functionality and also for acceptance by doctors, especially because results do not need to be transferred from an animal model to the human. It may also be advantageous if "negative learning" is facilitated when learning is carried out using tissue samples that are known to involve abnormal tissue (e.g., tumor tissue), and then, further analysis is performed in the application to determine whether the current tissue sample still belongs to the same class or may need to be assigned to a different class.

Training may be performed only when a specified target value is reached in the analysis. The target value may be specified by the surgeon, for example. If the specified target value is not reached during the analysis by the self-learning analysis unit, the training of the self-learning analysis unit effected by this analysis may be discarded. This has the advantage that intervention by the surgeon may adapt the reliability of the self-learning analysis unit more effectively (e.g., to a specific individual who is meant to undergo an operation).

The analysis unit uses at least two different models, where before the sensor signal is analyzed, the models are validated by checking a suitability of each of the models to the specific individual providing the tissue sample. Thus, this development provides the facility for one or more available models to be used preferentially for the analysis by the self-learning analysis unit. For example, the self-learning analysis unit may use the available models to examine the tissue sample by determining the relevant tissue type according to each model. The result may be verified by a third person (e.g., the surgeon). Based on this verification, the surgeon may then specify which of the models is meant to be used for further examinations or for determining tissue types. This may vary according to the individual.

The analysis unit may use for the analysis at least one weighting function. The weighting function may be used to take into account the relevance of a particular analysis result. The weighting function may either be specified by the surgeon or be set appropriately during the training.

Each model for the analysis may be assigned a dedicated weighting function. This option is intended particularly for the case in which the analysis unit uses two or more models rather than just a single model for analysis. The weighting function may assign an individual weighting to a particular model according to the relevance of the results obtained. The tissue type may thus be determined even more effectively.

In one embodiment, the tissue sample is exposed to definable electromagnetic radiation. The definable electromagnetic radiation may be infrared radiation, UV radiation, visible light, combinations thereof, and/or the like. The tissue sample may be exposed solely to monochromatic electromagnetic radiation, and the radiation sensor is not only sensitive to the monochromatic electromagnetic radiation but also detects other radiation bands. This allows detection of specific spectral changes, which may occur as a result of interactions of the tissue sample with the monochromatic electromagnetic radiation. It is thus possible to detect conversions, for example, in which the monochromatic electromagnetic radiation is changed spectrally at least partially by the tissue sample. Overall, the functionality of one or more of the present embodiments may thus be further improved.

The analysis unit may be formed by an electronic circuit, a processing unit, combinations thereof, and/or the like. The processing unit may be configured such that the processing unit may perform at least part of the method according to one or more of the present embodiments. The processing unit is controlled accordingly by the computer program. Both the processing unit and the electronic circuit may be formed by one or more semiconductor chips. The analysis unit may also be formed by discreet electronic components and combinations with semiconductor chips. For example, the analysis unit may include a memory unit, in which at least some of the training datasets may be stored. In addition, at least some of the computer program for the processing unit may be stored in the memory unit.

The aforementioned computer program product may be in the form of a computer-readable storage medium (e.g., a non-transitory computer-readable storage medium). In addition, the computer program may be loaded directly into an internal memory of the processing unit. It is thereby possible, for example, to download the computer program from a data source (e.g., a server) from within a network (e.g., the Internet) and to load the computer program into an internal memory of the processing unit in order that the processing unit may execute the computer program. The computer program product may include a computer-readable medium, on which the program code segments are stored. The computer-readable medium may be, for example, a memory chip (e.g., a PROM), a compact disk, a USB stick, or the like.

The advantages and effects defined for the method according to one or more of the present embodiments also apply equally to the use, to the computer program product, and to the device according to the present embodiments, and vice versa. Hence method features may also be worded as device features, and vice versa.

BRIEF DESCRIPTION OF THE DRAWINGS

Same features and functions are denoted by the same reference signs in the figures, in which:

FIG. 2 is a schematic flow diagram of a procedure for the method according to an embodiment.

DETAILED DESCRIPTION

Figure 1:
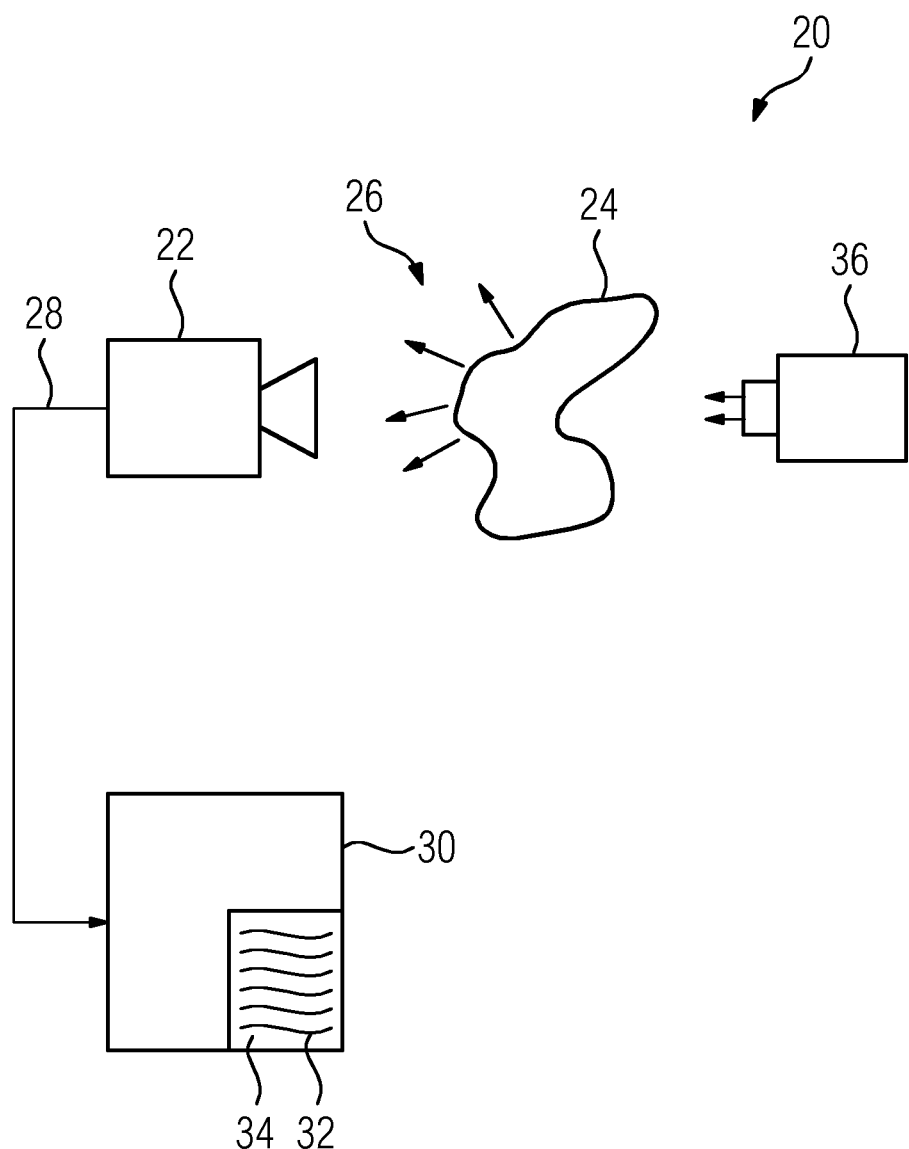
FIG. 1 is a schematic block diagram of a structure for performing a method according to an embodiment.

FIG. 1 shows, in a schematic block diagram, one embodiment of a device 20 for determining a tissue type of a tissue of an animal or a human individual. The device 20 includes a radiation sensor 22 for detecting electromagnetic radiation 26 emitted by a tissue sample 24 of the tissue. The radiation sensor 22 provides a sensor signal 28 according to the detected electromagnetic radiation. In the present case, the electromagnetic radiation 26 is infrared radiation. The radiation sensor 22 is accordingly configured as an infrared sensor.

The device 20 also includes an analysis unit 30 for analyzing the sensor signal 28. The sensor signal 28 is an electrical signal in the present case. The sensor signal 28 is also an analog signal, for example.

In order to determine the tissue type of the tissue sample 24, the analysis unit 30 is configured as a self-learning analysis unit 30. In addition, the self-learning analysis unit 30 has initially been trained based on at least one model using training datasets 32 stored in a database 34 of the analysis unit 30. In the present case, the model is a multilayer neural network that may be trained based on a machine learning method. The training of the analysis unit 30 is provided by the training datasets 32. The training datasets 32 each include a training sensor signal with an associated training tissue type.

FIG. 2 shows a schematic procedure for a method according to the present embodiments. The method starts in act 38. In the subsequent act 14, the analysis unit 30 is trained initially based on at least one model using the training datasets 32.

The method continues with act 18, which checks whether a tissue sample 24 is available. If there is no tissue sample, or no new tissue sample, available, then the method jumps to act 40, which terminates the method.

If a tissue sample 24, or a new tissue sample 24, is available, then in act 10, the radiation sensor 22 detects the electromagnetic radiation 26 (e.g., infrared light) emitted by the tissue sample 24. The radiation sensor 22 provides the sensor signal 28 according to the detected electromagnetic radiation 26.

The method 20 then continues with act 12, in which the analysis unit 30 analyzes the sensor signal 28 in order to determine the tissue type of the tissue sample 24. For this purpose, the sensor signal 28, which in the present case is an analog signal, is first digitized and input to digital signal processing by the analysis unit 30. For this purpose, the analysis unit 30 includes a processing unit (not shown further here), which is controlled by a suitably designed computer program in order to be able to implement the required functionality according to the present embodiments. The determined tissue type is output at the end of act 12. The output may be made acoustically, visually, or haptically (e.g., by loudspeaker reproduction, displaying on a monitor, by a light signal, by a vibration on an operating control, and/or the like).

The method continues with a branch operation 16, which checks whether the tissue type was determined with sufficiently high reliability. For this purpose, a surgeon (not shown) may specify a predetermined reliability value. If the tissue type is determined with correspondingly high reliability, the method branches to act 14, where the analysis unit 30 is retrained, taking into account the dataset newly obtained by determining the tissue type. If the predetermined reliability is not achieved, the method continues with act 40 and terminates.

For the act 14 of training, the self-learning analysis unit 30 may need a plurality of training datasets 32. It is often difficult, however, for approval of such a method, to obtain from human tissues a sufficiently large number of training datasets 32 to be able to provide a correspondingly well-founded database 34 for it to be possible to train the analysis unit 30 reliably.

The following additional acts may be provided in order to solve the problem mentioned above.

One first such act may be performed before the analysis unit 30 is first used (e.g., preoperatively). The analysis unit 30 is in this case trained initially from animal models.

For this purpose, infrared spectra may be determined from an animal model. The training datasets 32, which may be saved in the database 34, may be determined from these infrared spectra. The tissue samples 24 examined in this process may contain normal or healthy tissue (e.g., from the brain) and may also contain tumor tissue or abnormal tissue (e.g., of the same tissue type as for the healthy tissue; from a glioma, glioblastoma, and/or the like).

The spectra or sensor signals 28 acquired from the tissue samples of the animals (e.g., of the same species; from a rat, Sprague Dawley, or the like) may subsequently be analyzed and validated. For example, a histological examination may be performed.

The training datasets 32 obtained in this process from normal or healthy tissue and/or abnormal tissue (e.g., tumor tissue; of the same tissue type) may be added to the database 34.

In addition, different tissue types from another species (e.g., from Fischer rats or the like) may be taken into account. IStandardized animals that have been kept under standardized conditions may be used for creating the training datasets 32.

A further analysis and validation is performed on the additional training datasets 32 obtained for the different species of animals.

The training datasets 32 obtained in this process are subsequently added to the database 34. Domestic animals such as a dog, pig, cow, but also cat, mouse, and/or the like may also be used as the animals.

The training datasets 32 are re-validated, whereupon a corresponding database 34 is then created taking into account the training datasets 32 obtained in this process.

The database 34 may be expanded further by training datasets 32 that are provided (e.g., preoperatively) using tissue samples 24 from human tissue.

This may be done by providing suitable training datasets 32 using tissue samples 24 from human tissue (e.g., normal or healthy tissue; from the brain, or the like), abnormal tissue (e.g., tumor tissue; of the same tissue type; a glioma, a glioblastoma, and/or the like), and from different tissue types.

The training datasets 32 obtained accordingly in this process (e.g., actually acquired from the same individual or patient) are analyzed and validated. A comparison with the database 34 is then performed.

Then, a more extensive analysis and validation is performed on the training datasets 32 that have been acquired from different individuals or patients. Once again, a comparison with the database 34 is performed.

The training datasets 32 obtained in this process are added to the database 34.

The aforementioned procedure may hence be used to provide an initial database 34 capable of providing a multiplicity of training datasets 32 so that the analysis unit 30 may be trained initially.

The adaptation or training of the analysis unit 30 need not be concluded with the aforementioned procedure, however. The present embodiments allow relevant analysis models of the analysis unit 30 to be adapted even during use or while the method is being performed according to the present embodiments. It is thus possible, for example, to acquire different tissue samples from non-tumor tissue. The different tissue samples may act as internal references. For this purpose, the surgeon may specify the tissue type, so that a corresponding training dataset 32 may be provided accordingly.

The acquisition of the training datasets 32 obtained hereby may act as an additional internal reference, and a further comparison with the database 34 is performed.

Then, the surgical procedure or operation (e.g., removing a tumor) may begin, in which the tissue-type classification determined according to the invention may be used in order to control the surgical procedure or operation by the surgeon.

The hereby obtained control datasets in relation to known tissue types may be used in two ways.

One possibility is to perform a validation by first validating models before an operation or surgical procedure. In this case, the suitability of each of the models is checked for the specific patient or specific individual. Models having a prediction or classification that differs by more than a definable amount from the target value specified by the surgeon (e.g., tumor or non-tumor) may be ruled out for inclusion during the operation.

An alternative or additional possibility may be re-calibration and/or retraining. There are several possible ways to proceed here. In the simplest case, control datasets may be used for adapting a non-linear threshold-value or output function that maps a model output onto a classification decision. For example, a model prediction of say 10% tumor probability and a setting specified by the surgeon of 0% may cause an output value from the model to be corrected downwards. In another implementation, a weighting function that combines a plurality of models in a suitable manner may be trained. In this case, each model may be assigned a dedicated weighting or even a dedicated weighting function, which represents suitability for the specific surgical procedure or operation or for the specific individual. The weightings may be trained using control datasets such that a combined total value has a maximum match with the setting specified by the surgeon.

Since a number of training datasets 32 that may be determined during an operation, for example, will usually be relatively small, and therefore generally is unlikely to be sufficient for training the analysis unit 30, the following may also be provided.

The surgeon specifies as a test dataset a particular tissue type to be determined in conjunction with a test spectrum or test sensor signal to be classified. A suitable algorithm may then be used to obtain from the total set of all training datasets 32 in the database 34, a number of training datasets 32 that may be the most similar to the specified test dataset. A suitable similarity measure may be defined for this purpose. Such training datasets may number 500, for example.

The training datasets 32 determined during an operation may be added additionally to the training datasets 32 obtained in this manner. The portion of the database 34 formed thereby may then be used for training the analysis unit 30 (e.g., using a local model for classifying or determining the tissue type). Partial least squares, for example, may be used for this. The model obtained in this manner may then be validated and used for classifying the specified test dataset.

Using currently available hardware (e.g., also processing units), it may be possible to perform the method according to one or more of the present embodiments at a speed that makes usage possible for the surgeon even during an operation.

The training datasets determined during the operation may be stored and may be used with a suitable learning method even independently of a target value for training a model of the analysis unit 30. Semi-supervised learning methods and also methods from the field of deep learning (e.g., Restricted Boltzmann Machines) or the like may be used, for example, for this purpose.

The exemplary embodiments described above are used solely for explaining the invention and shall have no limiting effect on the invention. For example, the described method of the invention is not confined to classifying tissue types such as tumor or non-tumor. The described method may also be applied to predicting continuous variables or to a regression (e.g., a blood alcohol concentration), or the like.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining a tissue type of a tissue of an animal or a human individual, the method comprising:
    detecting, by a radiation sensor, electromagnetic radiation emitted by a tissue sample of the tissue, the radiation sensor providing a sensor signal according to the detected electromagnetic radiation; and training an analysis unit using at least one known dataset from the same animal or the same human individual before determining the tissue type of the tissue sample; and determining the tissue type as normal or abnormal, and outputting the tissue type, determining the tissue type comprising analyzing, by the analysis unit, the sensor signal, wherein the analysis unit is a self-learning analysis unit that is initially trained using training datasets based on at least one model based on a machine learning method, the training of the analysis unit being performed using the training datasets, each of the training datasets comprising a training sensor signal with an associated training tissue type, wherein after determining the tissue type of the tissue sample, the method further comprises retraining the analysis unit taking into account a dataset determined during a procedure, the dataset being associated with the determining of the tissue type of the tissue of the animal or the human individual, and wherein the retraining comprises:
reaching a specified target value in the determining of the tissue type of the tissue of the animal or the human individual; and
performing the retraining after the specified target value is reached.

2. The method of claim 1, wherein the tissue sample contains a marker agent that influences the electromagnetic radiation emitted by the tissue sample.

3. The method of claim 1, wherein the training datasets comprise specifiable training tissue types of animals, humans, or animals and humans, the specifiable training tissue types being associated with the training sensor signals.

4. The method of claim 3, wherein the specifiable training tissue types comprise healthy tissue, tumor tissue, or healthy tissue and tumor tissue.

5. The method of claim 1, wherein the analysis unit uses at least two different models, and
wherein the method further comprises validating the at least two different models before the analyzing of the sensor signal, the validating of the at least two different models comprising checking a suitability of each of the at least two different models to the specific individual providing the tissue sample.

6. The method of claim 1, wherein the analysis unit uses for the analysis at least one weighting function.

7. The method of claim 6, wherein each model of the at least one model for the analysis is assigned a dedicated weighting function.

8. The method of claim 1, wherein the tissue sample is exposed to definable electromagnetic radiation.

9. The method of claim 1, wherein retraining the analysis unit taking into account a dataset determined during a procedure comprises retraining the analysis unit taking into account a dataset determined during an operation.

* * * * *